United States Patent
Lee

(10) Patent No.: US 6,387,034 B1
(45) Date of Patent: May 14, 2002

(54) BRACHYTHERAPY TREATMENT PLANNING METHOD AND APPARATUS

(75) Inventor: Eva K. Lee, Atlanta, GA (US)

(73) Assignee: Georia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/375,515

(22) Filed: Aug. 17, 1999

Related U.S. Application Data

(60) Provisional application No. 60/096,730, filed on Aug. 17, 1998.

(51) Int. Cl.[7] .................................................. A61N 5/00

(52) U.S. Cl. ............................................................ 600/1

(58) Field of Search ............................. 600/1, 2, 3, 439

(56) References Cited

U.S. PATENT DOCUMENTS 5,205,289 A * 4/1993 Hardy et al. .................... 600/7
6,095,975 A * 8/2000 Silvern ........................... 600/3

OTHER PUBLICATIONS

Lee, Eva K., Slides from "Integer Programming Strategies In Solving Large—Scale Set Partition/Covering Problems", Given to Lucent Technologies, 1996.

Lee, Eva K., Talk on "Computational Experience with a General Purpose Mixed 0/1 Integer Programming Solver MIPSOL", Given at INFORMS Conference, May 1997.

Lightsey, Ed, "Theragenics: The Shooting Star of Georgia Stocks in '97 More Importantly, TheraSeed Offers New Hope for Men With Prostate Cancer", Health Care—Stocks, Georgia Trend, Nov. 1997.

Gallagher, Richard J., et al, "Mixed Integer Programming Optimization Models for Brachytherapy Treatment Planning", Daniel R. Masys, Ed., Proceedings of the 1997 American Medical Informatics Association Annual Fall Symposium, pp. 278–282, Oct. 25, 1997.

Lee, Eva K. et al., "Treatment Planning for Brachytherapy: An Integer Programming Model, Two Computational Approaches and Experiments on Permanent Prostate Implant Planning", Physics in Medicine and Biology, pp. 145–165, May 1998.

* cited by examiner

*Primary Examiner*—John P. Lacyk
*Assistant Examiner*—Brian Szmal
(74) *Attorney, Agent, or Firm*—Thomas, Kayden, Horstemeyer & Risley, LLP

(57) ABSTRACT

A brachytherapy treatment planning method and apparatus employs an integer linear programming model for the placement of seeds and branch-and-bound and genetic techniques for finding optimized solutions for seed placement problems based on the model. The model uses binary indicator variables to represent the placement or non-placement of seeds in a predetermined three-dimensional grid of potential seed locations. In preferred embodiments, the three dimensional grid of potential locations corresponds to intersections of a rectangular grid of holes from a template used to place the seeds with each of a number of parallel cross-sectional images of the tumor and surrounding tissue. The images themselves are discretized into a number of image points at a granularity which may or may not be equal to the granularity of the template. The dose delivered to each image point is modeled as a linear combination of the indicator variables. A system of linear constraints is imposed to attempt to keep the dose level at each image point within specified bounds. The branch-and-bound and genetic methods may either maximize the sum of rewards associated with achieving the specified bounds or minimize the sum of penalties associated with deviating from the desired bounds.

89 Claims, 8 Drawing Sheets

Pct contour pts greater than 250% PrDose

Pct contour pts greater than 100% PrDose

BRACHYTHERAPY TREATMENT PLANNING METHOD AND APPARATUS

This application claims priority from Provisional Application Ser. No. 60/096,730, filed Aug. 17, 1998. The entirety of that provisional application is incorporated herein by reference.

BACKGROUND

1. Field of the Inventions

The inventions are related to brachytherapy in general and are specifically related to the placement and dosage of radioactive materials for brachytherapy.

2. Related Art

Brachytherapy is a type of radiation therapy that involves the placement of radioactive sources (referred to herein as "seeds") either in tumors (interstitial implants) or near tumors (intracavity therapy and/or mold therapy). In this treatment approach, radiation from the radioactive sources is emitted outward and is limited to short distances. Thus, unlike external beam radiotherapy, where radiation must traverse normal tissue in order to reach the tumor, brachytherapy is much more localized and therefore reduces radiation exposure to normal tissue while allowing a higher radiation dose as compared to external beam radiotherapy. Brachytherapy has become increasingly popular for the treatment of early-stage prostate carcinoma; therefore, the present inventions will be discussed with reference to the treatment of a prostate tumor. However, those of skill in the art will recognize that the present inventions are not limited to treatment of prostate tumors and that many other uses of the inventions are possible.

In the past, a major limitation to the use of radioactive seed implants was the difficulty of accurately placing the seeds, which may number from approximately 40–100, in a designated geometric pattern. However, with the advent of imaging devices such as transrectal ultrasound (TRUS), it has become possible to image both the prostate and the radioactive seeds. This in turn allows a radiation oncologist greater control in the placement of seeds than had been possible. Seed implantation is commonly performed with a template 300 (a plastic slab with a rectangular grid of holes in it as shown in FIG. 3), which is attached to a TRUS transducer 410 and mounted on a transperineal implantation device 400 as shown in FIG. 4. The TRUS transducer 410 transmits images to a dedicated display unit. A series of transverse images are taken through the prostate, and the TRUS unit displays the template grid superimposed on the prostate image. Needles inserted at the appropriate grid positions enable seed placement in the target at planned locations.

The existence of a suitable procedure for accurately placing seeds raises a second issue: determining the optimal placement (also referred to as the configuration) of the seeds. The placement of seeds should be chosen to satisfy two criteria: a) the sufficiency of the radioactive dose received by the tumor; and b) the minimization of the radioactive dose received by surrounding healthy tissue. The large number of potential configurations means only a small fraction of configurations can be investigated manually.

A number of prior art techniques used to determine seed configurations have been used in the past, including the Manchester Paterson-Parker system, the Quimby system and the Paris system. One problem with these known methods is that they take a large amount of time (on the order of four hours or more) to perform. Thus, treatment strategies devised using these methods are typically generated in a simulation session several days (or weeks) before placement is to be performed. Unfortunately, it is often the case that the position of the diseased organ in the operating room differs from the position of the organ for which the treatment plan was intended. In such cases, it may be necessary to change the plan in the operating room. What is needed is a method and apparatus for quickly (i.e., within minutes) calculating a good brachytherapy treatment plan.

SUMMARY

The aforementioned need is met to a great extent by the present invention which provides an integer linear programming model for the placement of seeds and several techniques for finding optimized solutions for seed placement problems based on the model. The model uses binary (referred to herein as "0/1") indicator variables to represent the placement or non-placement of seeds in a predetermined three-dimensional grid of potential seed locations. In preferred embodiments, the three dimensional grid of potential locations corresponds to the intersections of the rectangular grid of holes of the template discussed above with each of a number of parallel "cuts" of the tumor and surrounding tissue imaged by an imaging device such as a TRUS or CT scanner. The images generated by the imaging device are discretized into a number of image points at a granularity which may or may not be equal to the granularity of the template. The dose delivered to each image point is modeled as a linear combination of the indicator variables. A system of linear constraints is imposed to attempt to keep the dose level at each image point within specified bounds. Branch-and-bound and genetic algorithms are provided to find optimized solutions based on the model. The branch-and-bound and genetic methods may either maximize the sum of rewards associated with achieving the specified bounds or minimize the sum of penalties associated with deviating from the desired bounds.

BRIEF DESCRIPTION OF THE DRAWINGS

The foregoing and other features and advantages of the inventions will be more readily understood with reference to the following drawings in which:

FIG. 3 is a front view of a needle template used in brachytherapy treatment.

DETAILED DESCRIPTION

Figure 1A:
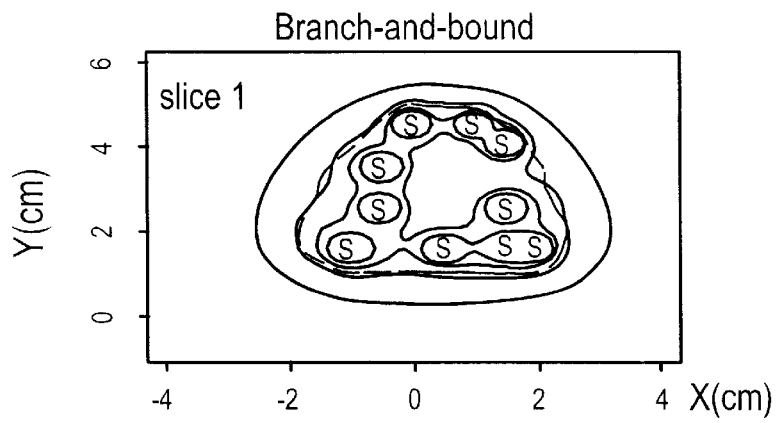
FIGS. 1a and 1n illustrate radiation isodose curves (solid curves) overlaid on prostate contours (dotted curves) for various slices of a patient prostate region for brachytherapy treatment plans obtained with branch-and-bound and genetic methods according to the present inventions.

The present inventions will be discussed with reference to preferred embodiments of methods for planning brachytherapy treatments. Specific details, such as the use of a prostate tumor to illustrate the methods, type of imaging device, specific dimensions, numbers of seeds, etc., are set forth in order to provide a thorough understanding of the present inventions. The preferred embodiments discussed herein should not be understood to limit the inventions.

In an ideal situation, it is desirable to develop a treatment plan that provides a sufficient radiation dose (as prescribed by the clinician) to the tumor region while sparing the neighboring healthy tissue from any radiation exposure. However, due to the close proximity of tumor regions and healthy tissue, such a treatment plan does not exist with today's technology. Clinically, in designing treatment plans, one strives to satisfy the prescription dose while providing minimal radiation to healthy, normal tissue. The methods discussed herein involve mixed integer programming problems. These problems, when solved to proven optimality, will produce optimal treatment plans which satisfy the clinical conditions imposed within the treatment planning models. However, since mixed integer programming problems are NP-hard, as of the date of this application there exists no known algorithm for solving mixed integer programs to proven optimality in "polynomial time." When exact algorithms (e.g., branch and bound) are applied to the MIP treatment planning models and are allowed to run to termination, optimal plans can be obtained. Nevertheless, with the present models, these algorithms can produce near-optimal plans quickly (within 5–15 minutes). Thus, the MIP approach enables clinicians to obtain high-quality treatment plans quickly and therefore handle unforseen situations arising during seed implantation. Therefore, when the terms "optimization" and "optimized" (and variants thereof) are used herein, what is being referred to is "near optimum," as in a near-optimum treatment plan.

Mixed Integer Programming Formulation

Basic Model

The mixed integer programming model tissue uses 0/1 variables to record placement or non placement of seeds in a predetermined three-dimensional grid of potential locations. The locations correspond to the intersections of the needles in the template used to place the seeds with each of a number of parallel cuts (imaged by an imaging device such as a TRUS or CT scan device) of the tumor site and neighboring healthy organs. If a seed is placed in a specific location, then it contributes a certain amount of radiation dosage to each point in the images. The images themselves are discretized at a granularity that is conducive both to modeling the problem accurately and to enabling computational approaches to be effective in obtaining solutions in a timely manner. In an application of the method to treat prostate carcinoma, points 2.5 mm apart were selected, resulting in approximately 800–1600 points within the images themselves, plus an additional 300–600 points representing the contours of the images.

The dose contribution of a seed to a point is calculated by assuming each seed is well approximated by a point source. In particular, at a distance r from a seed the dose contribution is given by:

$$D(r) = A\overline{T}\frac{F(r)}{r^2} \quad (1)$$

where A is the initial activity of the seed, $\overline{T}$ is the mean life of the radioisotope, and F(r) is the radial dose factor. In preferred embodiments, an appropriate table of dose factors associated with a discrete set of distances is selected (e.g., see Mohan and Anderson 1982*Memorial dose distribution computation service—Brachy II interstitial and intracavitary dose computation program user's guide* Memorial Hospital, Appendix I; Anderson et al. 1981, Clinical dosimetry with I-125, *Modern Interstitial and Intracavitary Radiation Cancer Management* George FW (Ed) Masson Publishing USA Inc. 9–15; 1993. A nomograph for permanent implants of Palladium-103 seeds *Int. J. Radiat. Onc. Biol. Phys.* 27 129–135, the contents of which are incorporated by reference herein), and linear interpolation is used to estimate dose factors for distances not in the table. The source emission is actually anisotropic. However, because the source orientation in the patient cannot be controlled, it is assumed that seeds are randomly oriented.

Given the grid of potential seed locations, the total dose level TD at each point P (in Euclidean coordinates) is given by:

$$TD(P) = \sum_{j=1}^{n} D(\|P - X_j\|)x_j, \quad (2)$$

where $x_j$ is a 0/1 indicator variable for recording placement or non placement of a seed in grid position j, $X_j$ is a vector corresponding to the coordinates of grid point j, n is the number of grid points (potential seed locations), and $\|\cdot\|$ denotes the Euclidean norm.

Associated with each point P are target lower and upper bounds, $L_P$ and $U_P$, on the total radiation dose delivered to point P. These bounds are commonly expressed as multiples of a desired prescription dose to the diseased organ, where all points in the same anatomical structure are assigned identical bounds.

Within this framework, the problem of finding a suitable configuration of seeds is interpreted as that of finding a solution to the following system of linear inequalities:

$$\sum_{j=1}^{n} D(\|P - X_j\|)x_j \geq L_P \quad (3)$$

$$\sum_{j=1}^{n} D(\|P - X_j\|)x_j \leq U_P,$$

where each of the variables $x_j$ is restricted to take on either 0 or 1. Unfortunately, it is not possible to satisfy all such inequalities simultaneously as discussed above. Indeed, due to the inverse square factor (see equation (1) above), the dose level contribution of a seed to a point less than 0.3 units away, for example, is typically larger than the target upper bound for the point.

The goal is to devise methods for assigning 0/1 values to the $x_j$'s so that the system is satisfied "to the greatest extent possible" as discussed above. It is natural to consider optimization techniques to achieve this goal. It is necessary to select some metric for gauging "goodness" of solutions before appropriate optimization techniques can be employed. Two general classes of objectives may be used:

(a) maximize the sum of rewards associated with achieving the desired bounds;

(b) minimize the sum of penalties associated with deviating from the desired bounds.

In preferred embodiments, objective (a) is implemented by introducing three nonnegative weights (rewards) for each point. If the dose delivered to point P is greater than or equal to the target lower bound, $L_P$, the objective value is incremented by $\alpha_P \geq 0$; if the dose delivered is less than or equal to the target upper bound, $U_P$, the objective value is incremented by $\beta_P \geq 0$; and finally, if the dose delivered satisfies both bounds, the objective value is incremented by $\gamma_P \geq 0$.

To implement objective (b), two nonnegative weights per point are used in preferred embodiments. If the dose delivered to a point does not satisfy one of the target bounds, a penalty, equal to the deviation from the target bound scaled by the appropriate weight, is added to the objective value. That is, if $TD(P)<L_P$, the objective value is incremented by $\alpha_P [L_P-TD(P)]$, where $\alpha_P \geq 0$. Similarly, if $TD(P)>U_P$, the objective value is incremented by $\beta_P [TD(P)-U_P]$, where $\beta_P \geq 0$. The bounds and weights used in a specific prostate cancer implementation are specified below in Tables 1 and 2.

Incorporating the Objectives

A mixed integer linear program (MIP) is an optimization problem where:
  some (possibly all) of the decision variables are restricted to be integer valued,
  the decision variables are constrained by a system of linear equations and/or inequalities, and
  the objective function to be maximized or minimized is expressed as a linear function of the decision variables.

In order to formulate the basic model outlined above in the mixed integer programming framework, additional variables are introduced to capture the objective goals. For objective (a), one needs to capture when a point satisfies the various bound conditions. Thus, the 0/1 variables $\upsilon_P$, $w_P$ and $z_P$ are introduced with the following interpretations:

$$\upsilon_P = \{1, \text{ if } TD(P) \geq L_P$$
$$\{0, \text{ otherwise}$$

$$w_P = \{1, \text{ if } TD(P) \leq U_P$$
$$\{0, \text{ otherwise}$$

$$z_P = \{1, \text{ if } L_P \leq TD(P) \leq U_P$$
$$\{0, \text{ otherwise}$$

Then the MIP (mixed integer program) for objective (a) (referred to herein as A) can be stated as:

maximize $\Sigma_P(\alpha_P \upsilon_P + \beta_P w_P + \gamma_P z_P)$ subject to $$\sum_{j=1}^{n} D(\|P - X_j\|)x_j + N_P(1 - \upsilon_P) \geq L_P \quad \text{(MIP A)}$$

$$\sum_{j=1}^{n} D(\|P - X_j\|)x_j + M_P(1 - w_P) \leq U_P$$

$$z_P \leq \upsilon_P$$

$$z_P \leq w_P$$

$$\upsilon_P, w_P, z_P, x_j \in \{0, 1\}$$

where $M_P$ and $N_P$ are suitably chosen positive constants (discussed further below). If a solution is found such that $\upsilon_P=1$, then the term $N_P(1-\upsilon_P)$ in the first inequality in (MIP A) is zero; and hence, the target lower bound for the dose level at point P is satisfied. Similarly, if $w_P=1$, the term $M_P(1-w_P)$ in the second inequality in (MIP A) is zero; and hence, the target upper bound for the dose level at point P is satisfied. Finally, if $z_P=1$, then both $\upsilon_P=1$ and $w_P=1$, and consequently, the dose level delivered to point P satisfies both bounds. The objective, maximize $\Sigma_P(\alpha_P \upsilon_P + \beta_P w_P + \gamma_P z_P)$, is what drives the optimization engine to assign a value of 1 to the variables $\upsilon_P$, $w_P$ and $z_P$. In particular, at optimality, the converse of each of the above conditional statements is true, provided the associated objective coefficient is strictly positive. Formally,
  if $\alpha_P>0$, then at optimality, $\upsilon_P=1$ if and only if the target lower bound at point P is satisfied;
  if $\beta_P>0$, then at optimality, $w_P=1$ if and only if the target upper bound at point P is satisfied; and
  if $\gamma_P>0$, then at optimality, $z_P=1$ if and only if the dose delivered to point P satisfies both bounds.

The argument to establish the "if" direction in each of the above statements is elementary. For example, consider the first statement. If the target lower bound at point P is satisfied, but $\upsilon_P=0$, then the current solution is not optimal since a better solution can be found by modifying the current solution. The modified solution is selected identical to the current solution except the variable $\upsilon_P$ is assigned the value 1 instead of 0. Thus, the modified solution has an objective value that exceeds the current (supposedly optimal) solution by $\alpha_P$.

The role of the constants $N_P$ and $M_P$ in (MIP A) is to ensure that there will be feasible solutions to the mathematical model. In theory, these constants should be chosen large enough so that if $\upsilon_P$ or $w_P$ is zero, the associated constraint in (MIP A) will be satisfied regardless of how the 0/1 variables $x_j$ are assigned. In practice, the choice is driven by computational considerations of the optimization algorithm being used and/or by decisions by the radiation oncologist. For the genetic algorithm described below, these constants are irrelevant since the algorithm does not depend on the constraints at all. For the branch-and-bound algorithm described below, the constants are needed, and it is advantageous computationally to assign values that are as small as possible. The radiation oncologist can guide the selection of the constants by either declaring absolute extremes on acceptable radiation dose levels delivered to each point (note that $U_P+M_P$ is the absolute maximum dose level that will be delivered to point P under the constraints of (MIP A), and $L_P-N_P$ is the absolute minimum), or by estimating the number of seeds needed for a given plan. In the latter case, if the number of seeds needed is estimated to be between 80 and 120, for example, then the constant $N_P$ can be taken to be $L_P$ minus the sum of the smallest 80 of the values $D(\|P-X_j\|)$, and the constant $M_P$ can be taken to be the sum of the largest 120 such values minus $U_P$. Selection in this fashion will ensure that no plan having between 80 and 120 seeds will be eliminated from consideration.

For objective (b), nonnegative continuous variables $\gamma_P$ and $z_P$ are introduced to capture the deviations of the dose level at a given point from its target lower and upper bounds, respectively. The MIP for objective (b) (MIP B) can be stated as:

maximize $\Sigma_P(\alpha_P \gamma_P + \beta_P z_P)$ subject to $$\sum_{j=1}^{n} D(\|P - X_j\|)x_j + \gamma_P \geq L_P \quad \text{(MIP B)}$$

$$\sum_{j=1}^{n} D(\|P - X_j\|)x_j - z_P \leq U_P$$

$$\gamma_P \geq 0, z_P \geq 0, x_j \in \{0, 1\}.$$

When applied to (MIP B), an optimization engine will attempt to assign values to the 0/1 variables (i.e., select seed positions from the set of potential seed positions) so that the weighted sum of deviations from the target bounds, $\Sigma_P(\alpha_P\gamma_P+\beta_P w_P)$, is minimized. Note that it is the objective that drives the optimization engine to select $\gamma_P$ and $z_P$ to represent the deviations. Indeed, at optimality, any constraint for which $\gamma_P$ ($z_P$) is non zero will be satisfied at equality, provided that $\alpha_P$ ($\beta_P$) is strictly positive.

In both models, the objective function weights ($\alpha_P$, $\beta_P$, $\gamma_P$) should be selected according to the relative importance of satisfying the associated bounds. For example, weights associated with an upper bound on the radiation dose for points in a neighboring healthy organ may be given a relatively larger magnitude than weights associated with an upper bound on the dose level for points in the diseased organ. In a similar spirit, the lower and upper bounds, $L_P$ and $U_P$, can be selected to guide the optimization engine to select solutions with desired characteristics. Given a target prescription dose for the diseased structure, the dose delivered to points on the boundary of the structure could be tightly controlled by appropriately selecting lower and upper bounds (e.g., 100% and 115% of the prescription dose) for points representing the contours of the structure, while other points within the diseased structure could be restricted by a much wider range of bounds (e.g., 100% and 160% of the prescription dose). In this way, the dose to tissue outside of the diseased structure is effectively controlled. The selection of a set of weights and bounds may be guided by analysis of solutions via other criteria, such as isodose curves and dose-volume histograms. Such criteria helped to influence the choice of weights and bounds for application of the models to the prostate cancer cases discussed herein.

Model Variations

Various simplifications to (MIPA) are possible depending on how the objective coefficients and bounds are selected. For example, if it is desired to add a reward only if both target bounds at point P are satisfied, then one would select $\alpha_P=0$, $\beta_P=0$ and $\gamma_P>0$. In this case, the variables $\upsilon_P$ and $w_P$ can be replaced with $z_P$ and the constraints $z_P \leq \upsilon_P$ and $z_P \leq w_P$ can be eliminated. Another opportunity for simplification may arise if P represents a point in healthy tissue. In this case it may be reasonable to assign $L_P=0$; then the variable $\upsilon_P$ and the constraints involving $\upsilon_P$ can be eliminated.

When the target bounds $L_P$ and $U_P$ are expressed as multiples of a target prescription dose, $T_P$, another natural approach is to capture the deviations from $T_P$ directly. In our model, this can be achieved by replacing constraints (3) with:

$$\sum_j D(\|P-X_j\|)x_j + \gamma_P = T_P \quad (4)$$

where $\upsilon_P$ is a continuous variable, unrestricted in sign. In the objective, one can then minimize the q norm of the vector $\gamma$ of all deviations; i.e., minimize $\|\gamma\|_q = (\Sigma_P |\gamma_P|^q)^{1/q}$.

Another enhancement that could be incorporated into any of the above models is the allowance of alternative seed types, or possibly same seed types but having different source activities. There are a variety of radioactive sources that are used for brachytherapy, including cesium-137, iridium-192, palladium-103, iodine-125, and gold-198, each of which has its own set of exposure rate constants. Typically, however, a single seed type is used in a given treatment plan. This fact is, in part, due to the difficulty of designing treatment plans with multiple seed types. The allowance of multiple seed types can easily be incorporated into the MIP model—one need only modify the total dose level expression (2) as:

$$\sum_j \sum_i D_i(\|P-X_j\|)x_{ij} \quad (5)$$

Here, $x_{ij}$ is the indicator variable for placement or non placement of a seed of type i in grid location j, and $D_i(r)$ denotes the dose level contribution of a seed of type i to a point r units away. In this case, a constraint restricting the number of seeds implanted at grid point j is also needed: $\Sigma_i x_{ij} \leq 1$. It remains to be tested whether the added flexibility of allowing multiple seed types will have a substantial impact on the number of points at which the target dose levels can be satisfied. Computationally, the optimization problem may prove to be more difficult due to the increased number of 0/1 variables.

Finally, the basic model also allows the incorporation of additional physical constraints. For example, one could incorporate constraints to control the percentage of each tissue structure satisfying the specified bounds. Alternatively, one could, if desired, constrain the total number of seeds and/or needles used.

Computational Techniques

Two computational methods have been applied to instances of the models presented in the previous section to find an optimized solution. The first method, known as branch-and-bound, is an exact method commonly employed in solving integer programming problems. A branch-and-bound algorithm will, if allowed to run to completion, terminate with an optimal solution. Moreover, the "intelligent" search mechanism of the branch-and-bound method enables large sections of the solution space to be eliminated from consideration (knowing that no solution within can be optimal) without actually examining each solution within—thereby conserving computing time.

The second approach is a genetic algorithm. A genetic algorithm is a heuristic procedure, and is applied in this case without taking into account any constraints in the model. It is based on the idea of randomized enumeration, where the randomization is guided by operations designed to mimic the phenomena of crossover and mutation that naturally occur in the reproduction of species. The notion that only the best fit individuals survive to pass on their genetic material is mimicked by biasing the selection of parents by using a "fitness" function based on the objective function that is to be optimized. Although genetic algorithms have been applied with some success to combinatorial optimization problems, they are only heuristic search strategies. No test for optimality is embedded into a genetic algorithm. The user of the algorithm dictates that the algorithm should terminate either after a specified number of generations, or after the observed change in fitness scores between consecutive generations remains sufficiently small.

Branch-and-Bound Method

The classical approach to solving linear 0/1 mixed integer programs is branch-and-bound. This is a tree search approach where, at each node of the tree, certain binary variables are fixed to zero or one, and the remaining binary variables are relaxed (i.e., allowed to assume any value between zero and one). This results in a linear program (LP) being associated with each node of the tree. The LP at the root node is simply the original 0/1 MIP instance with all of the binary variables relaxed. The tree is constructed such that the binary variables fixed in a parent node will be fixed identically in any of its children, and each child will have an additional binary variable fixed to zero or one. Typically, children are formed in pairs as follows. Assume that the LP at a given node is solved, and one or more of the relaxed binary variables is fractional in the optimal solution. One selects such a fractional binary variable and branches on it. That is, two child nodes are formed; one with the selected binary variable fixed to zero, and the other with the selected binary variable fixed to one. Of course, each child also inherits all of the fixed binary variables of its parent. Note that the objective value of a child node can be no greater (in the case of maximization) than the objective value of its parent.

If the linear program at a given node is solved and the optimal solution happens to have integral values for all the relaxed binary variables, then this solution is feasible for the original 0/1 mixed integer program. Once a feasible solution for the original problem is found, the associated objective value can be used as a lower bound (in the case of maximization) for the objective values of LP's at other nodes. In particular, if an LP at another node is solved, and its objective value is less than or equal to the lower bound, then none of its children could yield a feasible solution for the original MIP with a greater objective value than the one already obtained. Hence, no further exploration of this other node is needed, and the node is said to be fathomed.

Two other criteria for fathoming a node are obvious: if the associated LP is infeasible, or if the optimal solution of the LP has integral values for all relaxed binary variables, then no further exploration of the node is required. In the latter case, the optimal objective value of the LP will be compared with the current lower bound, and the lower bound will be updated if needed. The tree search ends when all nodes are fathomed.

A variety of strategies have been proposed for intelligently selecting branching variables and nodes to process. However, no strategy stands out as being best in all cases. What has become clear from recent research in computational MIP, is that branch-and-bound is most effective when coupled with other computational devices, such as problem preprocessing, primal heuristics, global and local reduced-cost fixing, and cutting planes. The reader can refer to the article by Lee and Mitchell (1999, Branch-and-bound methods for integer programming *Encyclopedia of Optimization* Floudas C A and Pardalos P M (Eds.) (The Netherlands: Kluwer Academic Publishers), the contents of which are incorporated by reference herein), for a concise description of branch-and-bound methods for integer programming. The books by Schrijver (1986, *Linear and Integer Programming* (New York: Wiley)), Nemhauser and Wolsey (1988, *Integer and Combinatorial Optimization* (New York: Wiley)) and Parker and Rardin (1988, *Discrete Optimization* (New York: Academic Press), the contents of which are incorporated by reference herein), contain detailed expositions on integer programming and related computational issues.

The numerical work of the preferred embodiments discussed herein is based on a branch-and-bound MIP solver that is built on top of a general-purpose mixed integer research code (MIPSOL) (Lee 1997, Computational experience of a general purpose mixed 0/1 integer programming solver, Technical Report School of Industrial and Systems Engineering Georgia Institute of Technology, the contents of which are incorporated by reference herein). The general-purpose code, which incorporates all of the above mentioned computational devices, has been shown to be effective in solving a wide variety of large-scale real-world MIP instances. A complete description of the solver and comparisons between numerical strategies are described in Lee et al. (1998a, Computational issues for a mixed integer programming approach to treatment plan optimization for radiation therapy, Technical Report School of Industrial and Systems Engineering Georgia Institute of Technology; 1998b, Mixed integer programming approaches to treatment planning for brachytherapy—application to permanent prostate implants, Technical Report School of Industrial and Systems Engineering Georgia Institute of Technology, the contents of which are incorporated by reference herein).

Genetic Method

A genetic algorithm is a heuristic optimization method modeled on the biological mechanisms of evolution and natural selection (e.g., see Buckles 1992, *Genetic Algorithms* (Los Alamitos, Calif.: IEEE Computer Society Press); Wasserman 1993, *Advanced methods in neural computing* (New York: Van Nostrand Reinhold, the contents of which are all incorporated by reference herein). In nature, the characteristics of an organism are encoded in streams of DNA known as chromosomes. Likewise, in a genetic algorithm, a potential solution to a problem is encoded as a stream of symbols over a given alphabet. Given an initial population of individuals (i.e., potential solutions encoded as symbol streams), a subset of the population is selected to parent offspring for the next generation. The parent selection process is stochastic, but biased towards selecting those individuals that are most fit, as measured by a pre-selected fitness function (e.g., the objective function that one is trying to optimize).

After the parents are selected, they are paired off and mated. That is, subsections of two parent symbol streams are interchanged, forming two new members for the next generation. This is analogous to cross-over in biological reproduction, where a child's genetic composition is a combination of its parents. Mutations are also possible. This is typically implemented by randomly selecting a child symbol stream and randomly altering one of its symbols.

The algorithm can be terminated after a specified number of generations have been created (usually several hundred), or by examining when the difference between the maximum and minimum fitness values between consecutive generations remains less than a specified threshold for a number of generations. Upon termination, the individual in the final generation with the largest fitness value is selected as the operative solution to the problem at hand.

Obviously, many variations on implementation specifics for a genetic algorithm are possible. For the case at hand, a given seed configuration can be viewed as a stream of 0's and 1's. In terms of the notation in the previous section, such a stream is analogous to an instantiation of the binary variables $x_j$.

The genetic algorithm described herein begins by randomly generating 600 binary data streams of length n, all having the same number of 1's (an initial estimate of the number of seeds required). From this set of 600, the top scoring 15, excluding duplicates, are selected for the first generation. Subsequent generations all have 15 members as well. To create the next generation from the current generation, 14 of the 15 data streams are selected to be involved in a crossover and paired up. For the crossover operation, non-contiguous randomly selected bits are interchanged. A uniformly distributed random number between 0 and n/2 is used to determine the number of bits to be interchanged between parent pairs.

After cross-over occurs, the mutation operation is performed five times. Each operation involves randomly selecting one of the 15 data streams (14 newly created data streams resulting from crossover, plus the one data stream that was not selected to be a parent) and randomly selecting a bit to be inverted. Note that the same data stream could be selected two or more times for mutation, and, though unlikely, one mutation could cancel the effect of a previous mutation.

In order to ensure that the current best solution is not lost, the strategy of elitism is employed. That is, the data stream with the highest fitness value is passed on unchanged to the next generation. This is implemented by simply overwriting one of the newly created children. More details on the implementation of the genetic algorithm can be found in Silvern (1998, Automated OR prostate brachytherapy treatment planning using genetic optimization, Ph.D. Thesis, Department of Applied Physics, Columbia University, New York, the contents of which are incorporated by reference herein).

Numerical Experiments

Data from 20 prostate cancer patients were used to test the models and algorithmic approaches discussed above. The data included points representing the discretization of three anatomical structures—the prostate, the rectum, and the urethra. Two distinct categories of points were used to represent the prostate. Contour points specified the boundary of the prostate in each of the images; and the regions determined by each boundary were populated with uniformly spaced points, referred to herein as uniformity points. Within each image, both the contour points and the uniformity points were spaced 2.5 mm apart in each dimension. The images themselves were spaced 5 mm apart. In addition to the discretization data, isotope source activities and radial dose factors, and coordinates of potential seed locations were also specified.

The results described herein facilitate two objectives: (1) to assess the effects of using the different models and model parameters, and (2) to compare plans obtained by the branch-and-bound optimization approach to those obtained by the genetic algorithm approach. To facilitate objective (1), a single optimization algorithm (the branch-and-bound algorithm) was applied to each model and the objective weights were varied in an identical manner across models. Comparison between treatment plans was based on quantitative measures of the percentage of points in each anatomical structure achieving specified target dose bounds, as well as by visual inspection of dose-volume histograms and isodose curves. To facilitate objective (2), a single model and objective weight combination was selected for each method, and each method was applied to all 20 patient cases. Comparison between treatment plans obtained with the two methods was performed using the same criteria as in goal (1).

Choice of Model Parameters

The models described above offer many degrees of freedom for assigning target bounds and objective function weights. For example, each point in the discretization can be assigned its own unique set of bounds and weights. In preferred embodiments, however, it is reasonable to stratify the assignment of bounds and weights by point type. Thus, for each point type (i.e., contour, uniformity, rectum, and urethra), a target lower bound, a target upper bound, and three objective function weights were assigned.

The target bounds used are shown in Table 1. They are expressed as multiples of the

TABLE 1

|   | Rectum | Urethra | Uniform | Contour |
|---|--------|---------|---------|---------|
| L | 0.00   | 1.00    | 1.00    | 1.00    |
| U | 0.78   | 1.50    | 1.60    | 1.60    | target prescription dose to the prostate, which was patient dependent. Note that the lower bound for rectum points was set to zero, since there is no therapeutic reason to deliver any radiation to the rectum. In contrast, since the urethra is surrounded by the prostate, too little dosage to the urethra may be indicative that diseased tissue proximal to the urethra is not receiving adequate dosage. Hence, a positive-valued lower bound for urethra points was specified. One may argue that there is no therapeutic reason to place upper bounds on the dose delivered to points representing the prostate. However, from the optimization standpoint, there is an important reason. If no upper bounds are specified, the optimization engine will be guided by an objective that emphasizes the satisfaction of lower bounds, and thus will steer towards solutions that have an over abundance of seeds. The upper bounds on uniformity and contour points effectively help to limit the number of seeds selected, and thereby confine the prescription dose to the diseased tissue.

Extensive computational experiments were performed to study the effects of using different objective function weights for the various point types. Initial observations revealed that it was advantageous to assign weights based, at least in part, on the number of points in the discretization of each "structure." Here, we summarize results for the weight combinations given in Table 2. The symbols $n_r$, $n_{ur}$, $n_{un}$, and $n_c$ denote, respectively, the

TABLE 2

| Combination | Parameter | Rectum | Urethra | Uniform | Contour |
|-------------|-----------|--------|---------|---------|---------|
| 1 | α | 0 | $n_{un}/n_{ur}$ | 1 | $n_{un}/n_c$ |
|   | β | $n_{un}/n_r$ | $n_{un}/n_{ur}$ | 1 | $n_{un}/n_c$ |
|   | γ | 0 | 0 | 0 | 0 |
| 2 | α | 0 | $n_{un}$ | 1 | 1 |
|   | γ | $n_{un}$ | $n_{un}$ | 1 | 1 |
|   | γ | 0 | 0 | 0 | 0 |
| 3 | α | 0 | 0 | 0 | 0 |
|   | β | 0 | 0 | 0 | 0 |
|   | γ | $n_{un}/n_r$ | $n_{un}/n_{ur}$ | 1 | $n_{un}/n_c$ |
| 4 | α | 0 | 0 | 0 | 0 |
|   | β | 0 | 0 | 0 | 0 |
|   | γ | $n_{un}$ | $n_{un}$ | 1 | 1 | number of rectal points, the number of urethra points, the number of uniformity points, and the number of contour points. For the 20 cases considered, $n_{un}$ ranged between 568 and 2206, $n_c$ between 261 and 692, and $n_r$ and $n_{ur}$ between 6 and 10. (In each image, the positions of the rectum and urethra were each represented by a single point.)

Combinations 1 and 3 correspond to giving equal weight to each structure by taking into account how many points represent each structure. The uniformity points are the most numerous, so each uniformity point is weighted by 1, and each non uniformity point is weighted by the number of uniformity points divided by the number of points representing the associated structure. In combinations 2 and 4, each point representing the prostate is weighted by 1, and the rectum and urethra points are weighted by the number of uniformity points. The use of the large weights on rectum and urethra points in Combinations 2 and 4 greatly increases the likelihood that the optimization engine will select a solution for which the dose delivered to these points will be within the target bounds.

Including both combinations 1 and 2 (and similarly, 3 and 4) the numerical tests provided a way of gauging the sensitivity of treatment plans obtained to relatively small changes in contour point priority. The motivation for weighting contour points higher is to drive the optimization engine to select a solution in which the target prescription dose conforms well to the prostate, thereby reducing excessive exposure to nearby healthy tissue. In the 20 cases considered, the ratios $n_{um}/n_c$ ranged between 1.98 and 3.41, so the shift in priority is relatively small. Finally, the relative importance of allocating rewards (penalties) for satisfying (violating) bounds separately versus satisfying both bounds simultaneously can be analyzed by comparing results of using weight combinations 1 and 3, as well as weight combinations 2 and 4.

Note that all four weight combinations are directly applicable to (MIP A), whereas only combinations 1 and 2 are directly applicable to (MIP B). However, combinations 3 and 4 could be applied to a modified form of (MIP B) involving additional constraints and variables. Also note that since the lower bound for rectal points is set to zero (see Table 1), these points always achieve the lower bound; and consequently, there is no need to allocate a positive reward to the a parameter for the rectum in combinations 1 and 2.

Numerical Results

All treatment plans discussed herein were generated on 166 Mhz machines. Plans from the branch-and-bound algorithm were those associated with the first feasible solutions found (i.e., integer-valued, but not necessarily optimal), and were obtained within 300 CPU seconds. For the genetic algorithm, typically 1000 generations were used for generating a treatment plan, requiring approximately 900 CPU seconds.

For the evaluation of treatment plans, a much finer grid (1 mm spacing in each dimension) of uniformity points was used. This not only helped to obtain a more complete representation of dose delivered to the prostate, it also helped to eliminate the bias of testing a plan with the same data used to generate it. Plans were also evaluated using a smaller upper bound on the contour points than used in the models themselves. Visual inspection of isodose curves and dose-volume histograms showed that plans for which a significant number of contour points were within 115% of the prescription dose conformed quite well to the prostate volume. Hence, although the models upon which the plans were generated used an upper bound of 1.6 times the prescription dose, a factor of 1.15 was used in the evaluation phase.

In both (MIP A) and (MIP B), the initial plans obtained using weight combination 2 satisfied more bound conditions for urethra and rectum points than those obtained using weight combination 1. In (MIP A2) (i.e., (MIP A) with weight combination 2) 100% of the urethra and rectum points satisfied both bounds in 17 cases, while in the remaining 3 cases, approximately 80% of the points satisfied both bounds. In contrast, for (MIP A1) only 8 cases achieved 100% satisfaction of both bounds. In the remaining 12 cases, the percentage of points satisfying the upper bound ranged from 50–100%, and the percentage of urethra points satisfying the lower bound ranged from 80–100%. (Again, rectal points automatically satisfy their specified lower bound of zero.) For (MIP B2), in all 20 cases, all urethra points satisfied the lower bound and over 85% of rectum and urethra points satisfied the upper bound. For MIP B1), in 19 cases, all urethra points satisfied the lower bound, and in all 20 cases, between 40–85% of urethra and rectum points satisfied the upper bound. There are two factors contributing to the observed results. First, and likely more important, the urethra and rectum points are weighted significantly heavier in combination 2 than in combination 1. Second, the contour points are weighted somewhat less in combination 2 than in combination 1. Thus, for (MIP A2) and (MIP B2) the optimization engine will tend to select solutions in which the urethra and rectum points satisfy their bounds, and at the same time give relatively less emphasis (compared with (MIP A1) and (MIP B1)) to contour point bounds.

By the same token, one would expect more contour points to satisfy the measured bounds when using weight combination 1 than when using weight combination 2. We observed this to a small degree for (MIP A), but since the ratios $n_{um}/n_c$ were typically 3 or less, there was not a great difference. Among the 20 cases, for (MIP A1) on average 31% of contour points satisfied both bounds, 53% satisfied the upper bound, and 79% satisfied the lower bound. The corresponding percentages for (MIP A2) were 28%, 51%, and 77%. In 16 cases, there were at least as many contour points satisfying both bounds for (MIP A1) as there were for (MIP A2). The increase in the percentage of points satisfying both bounds ranged from 0% (5 cases) to 12%. In the four remaining cases, there were modestly more contour points (less than 2%) satisfying both bounds in (MIP A2) than in (MIP A1). In 14 cases, the percentage of contour points with dose level less than the upper bound was higher (by 0%–13%) in (MIP A1) than in (MIP A2), while in 6 cases it was lower (by 0%–4%). Perhaps more significant, the percentage of contour points at a dose level greater than 250% of the prescription dose was lower (by 0.3%–2.5%) in every patient case in (MIP A1) compared to (MIP A2). These results provide evidence to support the hypothesis that (MIP A) allows fairly fine-grain control of dose to contour points via incremental changes in weights associated with satisfying contour point bounds.

The results regarding contour points for (MIP B) under weight combinations 1 and 2 were mixed. In particular, weight combination 1 did not, in general, lead to the satisfaction of more bound conditions on contour points than did weight combination 2. This, together with the discussion in the previous paragraph, suggests that results of small weight adjustments to (MIP B) are less predictable than those to (MIP A).

The primary issue for uniformity points concerns the satisfaction of the lower bound so as to ensure the prostate receives a fall tumoricidal dose. For all models and weight combinations, on average 96%–97% of uniformity points achieved a dose level greater than or equal to the prescription dose. Of particular interest, however, is that there was one patient case (Patient 17) in which all models scored well below average (83%–87%). This anomaly occurred for the genetic algorithm as well as the branch-and-bound algorithm (see Table 3 and FIG. 2). Visual inspection of the contours for this case showed that they tapered off unusually sharply at both ends. The fact that all models and weight combinations returned similar results for this case suggests that this distinguishing physical feature of the prostate makes it significantly more difficult to find a plan with "desired" characteristics.

When the branch-and-bound algorithm was applied to (MIP A) using weight combinations 3 and 4, among the 20 patient cases, on average only 50% of the uniformity points satisfied the lower bounds, and less than 10% of the contour points were within both bounds (approximately 8% satisfied the lower bound, while over 90% satisfied the upper bound). These results suggest that initial solutions obtained from the branch-and-bound algorithm for these latter weight combinations yield plans that are inferior to those obtained via weight combinations 1 and 2. Overall, for the 20 cases considered, the best treatment plans generated from the branch-and-bound algorithm resulted from its application to (MIP A1).

In contrast, empirical tests using the genetic algorithm showed that, among the weight combinations used to test it, it yielded the best plans when applied to (MIP A) and a variant of weight combination 3 in which the γ parameters were set to 35, 40, 1, and 3 for the rectum, urethra, uniformity, and contour points, respectively (Silvern 1998, Automated OR prostate brachytherapy treatment planning using genetic optimization, Ph.D. Thesis, Department of Applied Physics, Columbia University, New York). Table 3 shows a comparison of plans from the branch-and-bound algorithm applied to (MIP A1) and the genetic algorithm applied to (MIP A) using the above weights. Patient cases are categorized according to the prescription dose. The source activity of seeds used is specified in the column labeled Activity. For each algorithm, the first three columns—labeled 100%, ≦115%, ≧250%—correspond to the percentage of contour points satisfying at least 100%, at most 115%, and above 250% of the prescription dose, respectively. Next, the column ≧100% indicates the percentage of uniformity points satisfying at least 100% of the prescription dose. Finally, No. Seeds denotes the number of seeds used in the generated plans.

branch-and-bound algorithm than for plans obtained via the genetic algorithm. This suggests that the former approach may provide better control on irradiation to external healthy tissue.

Figure 1B:
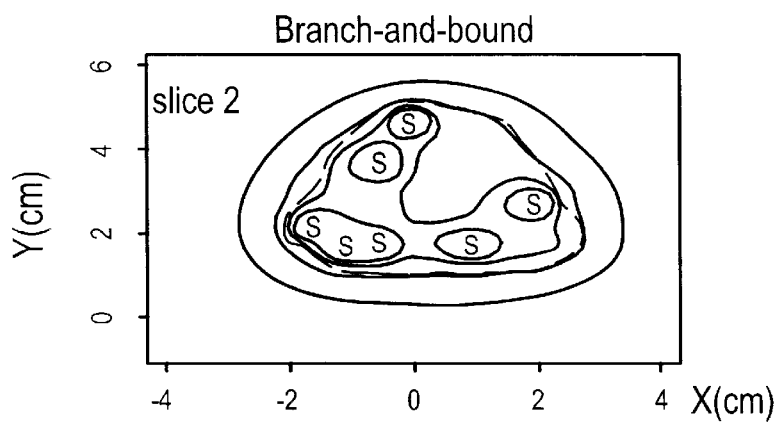
Figure 1C:
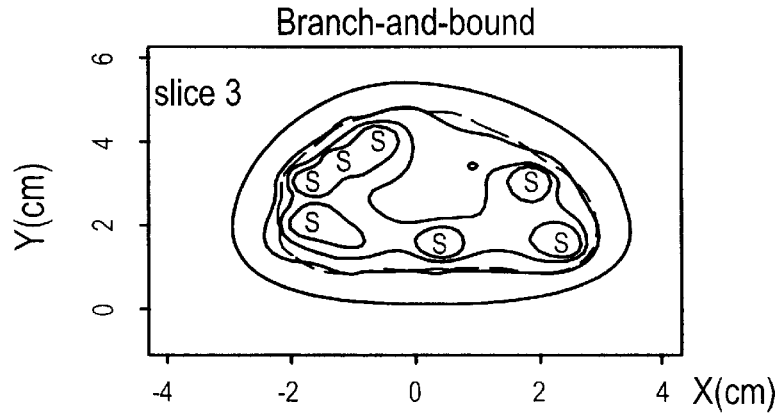
Figure 1D:
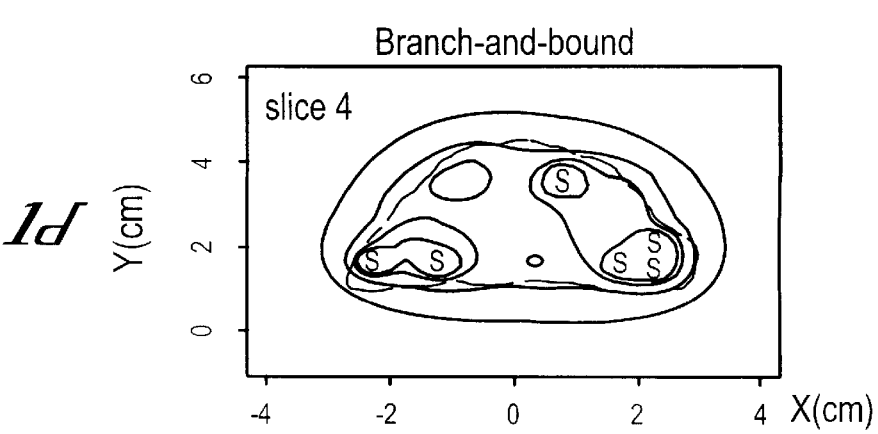
Figure 1E:
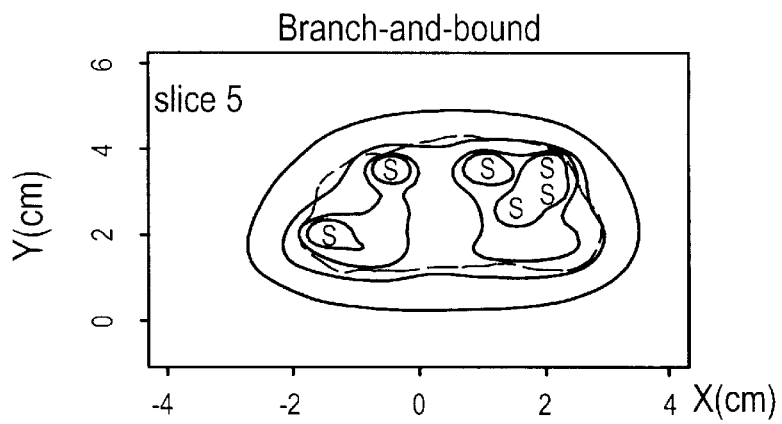
Figure 1F:
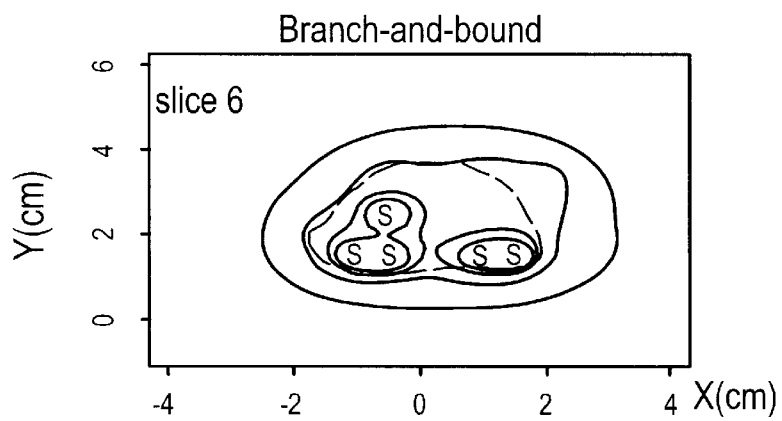
Figure 1G:
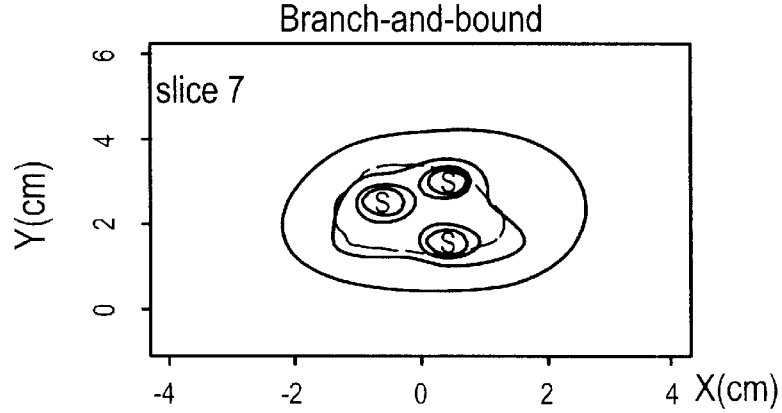
Figure 1H:
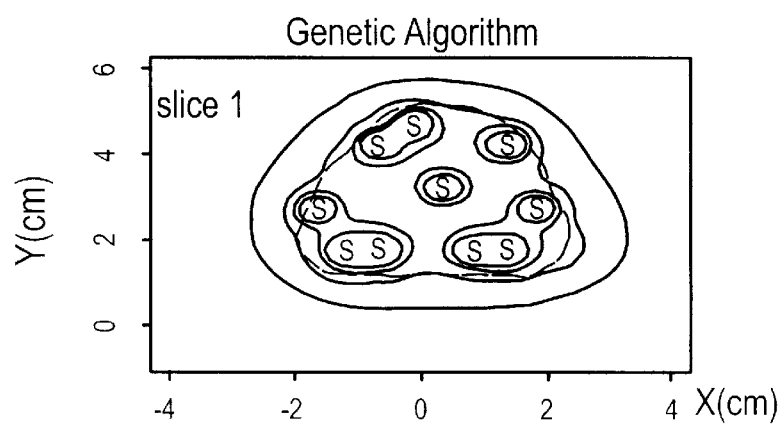
Figure 1I:
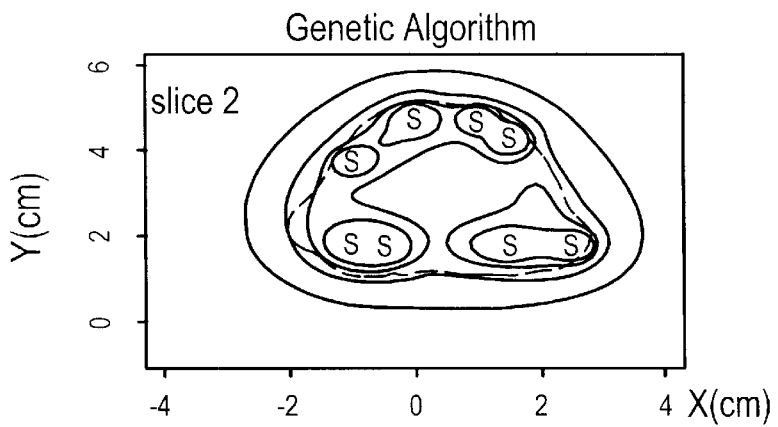
Figure 1J:
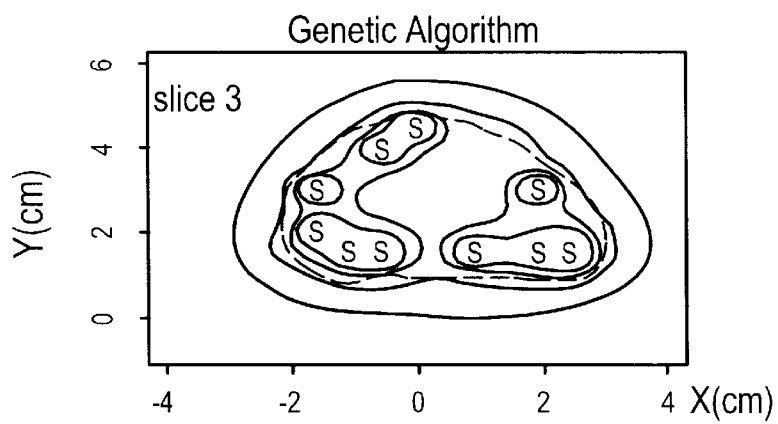
Figure 1K:
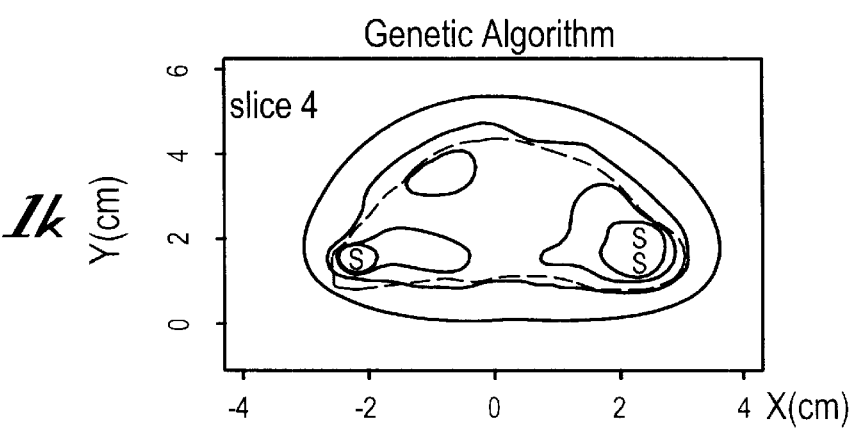
Figure 1L:
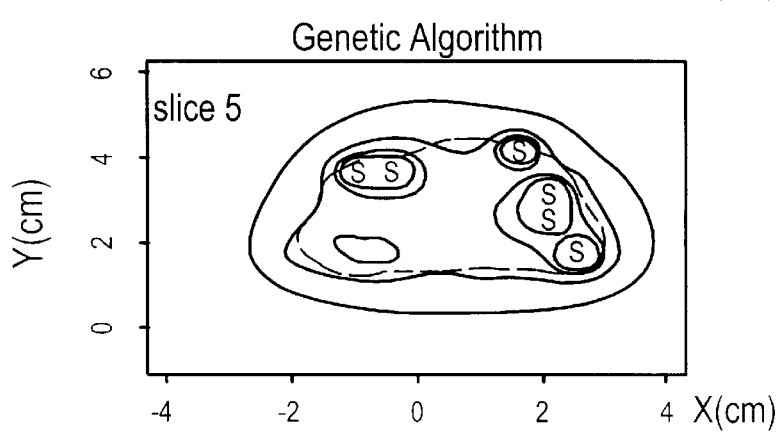
Figure 1M:
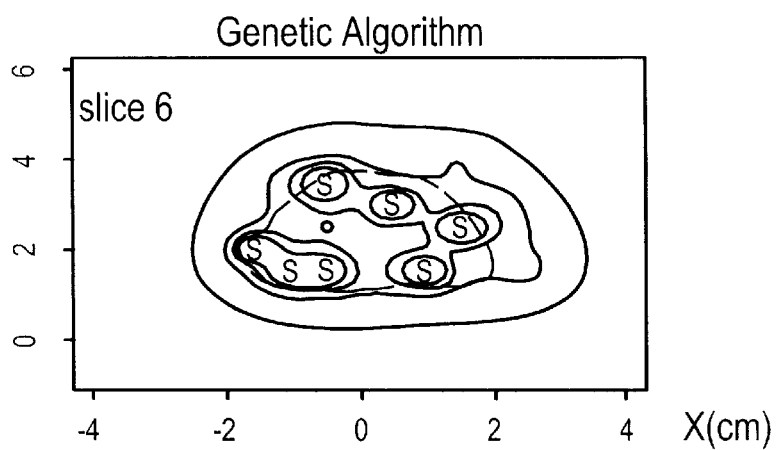
Figure 1N:
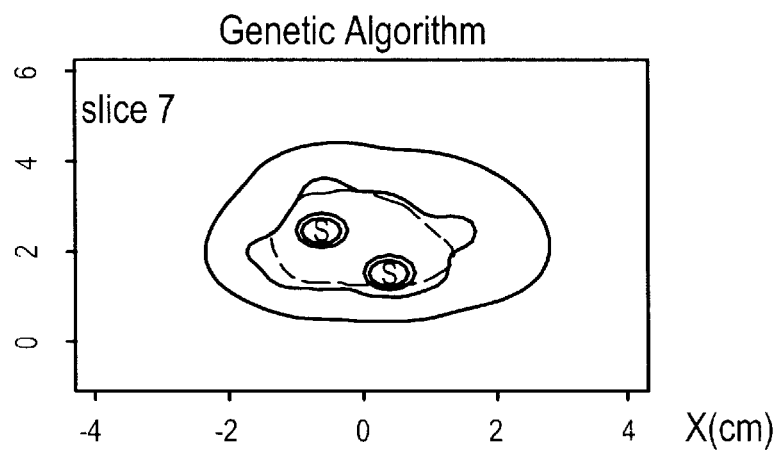
Figure 2A:
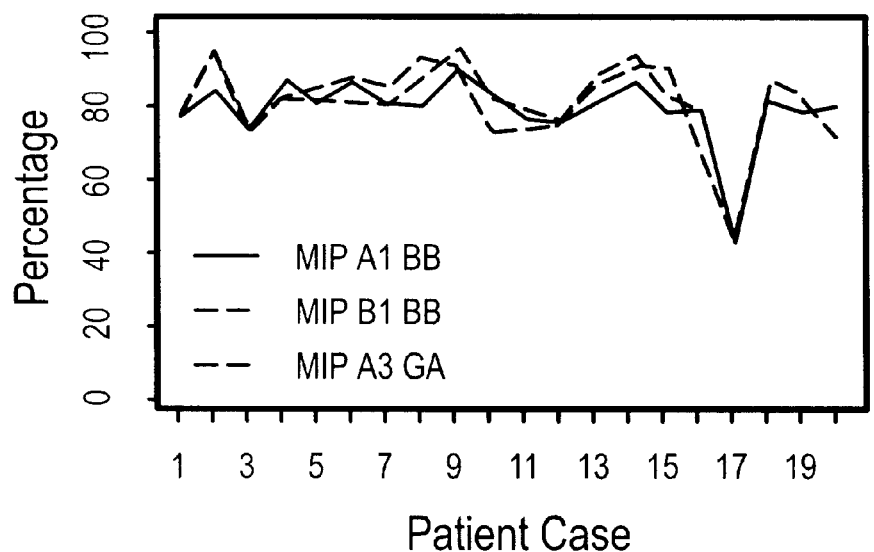
FIGS. 2a–2d are graphs showing the performance of various embodiments of brachytherapy treatment planning methods according to embodiments of the present inventions.
Figure 2B:
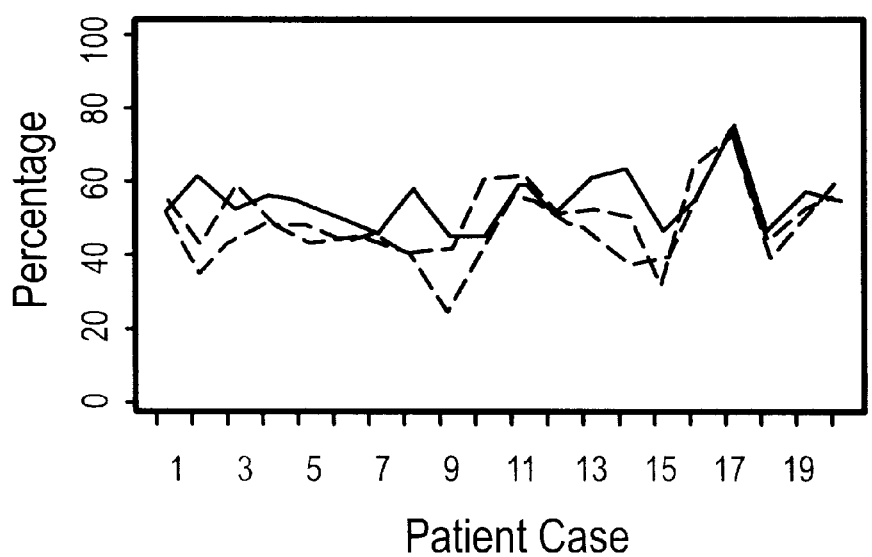
Figure 2C:
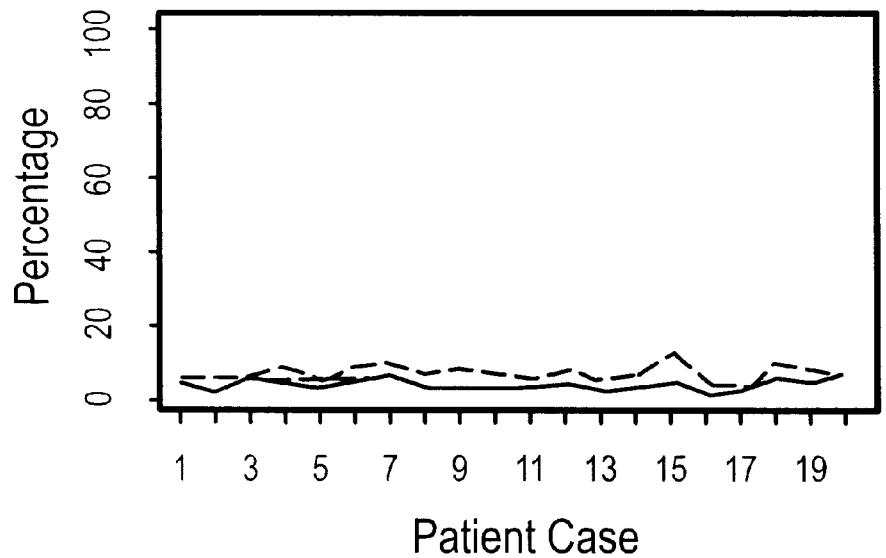
Figure 2D:
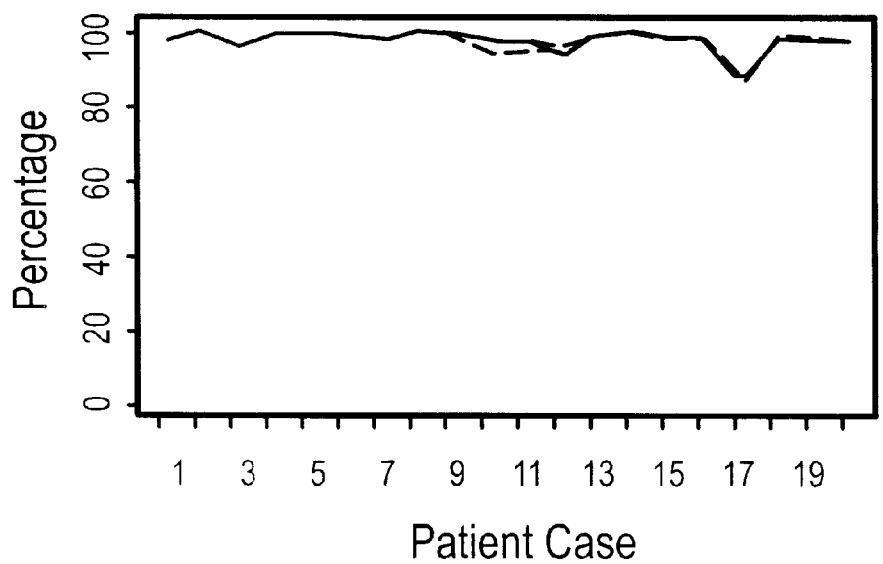
Figure 7:
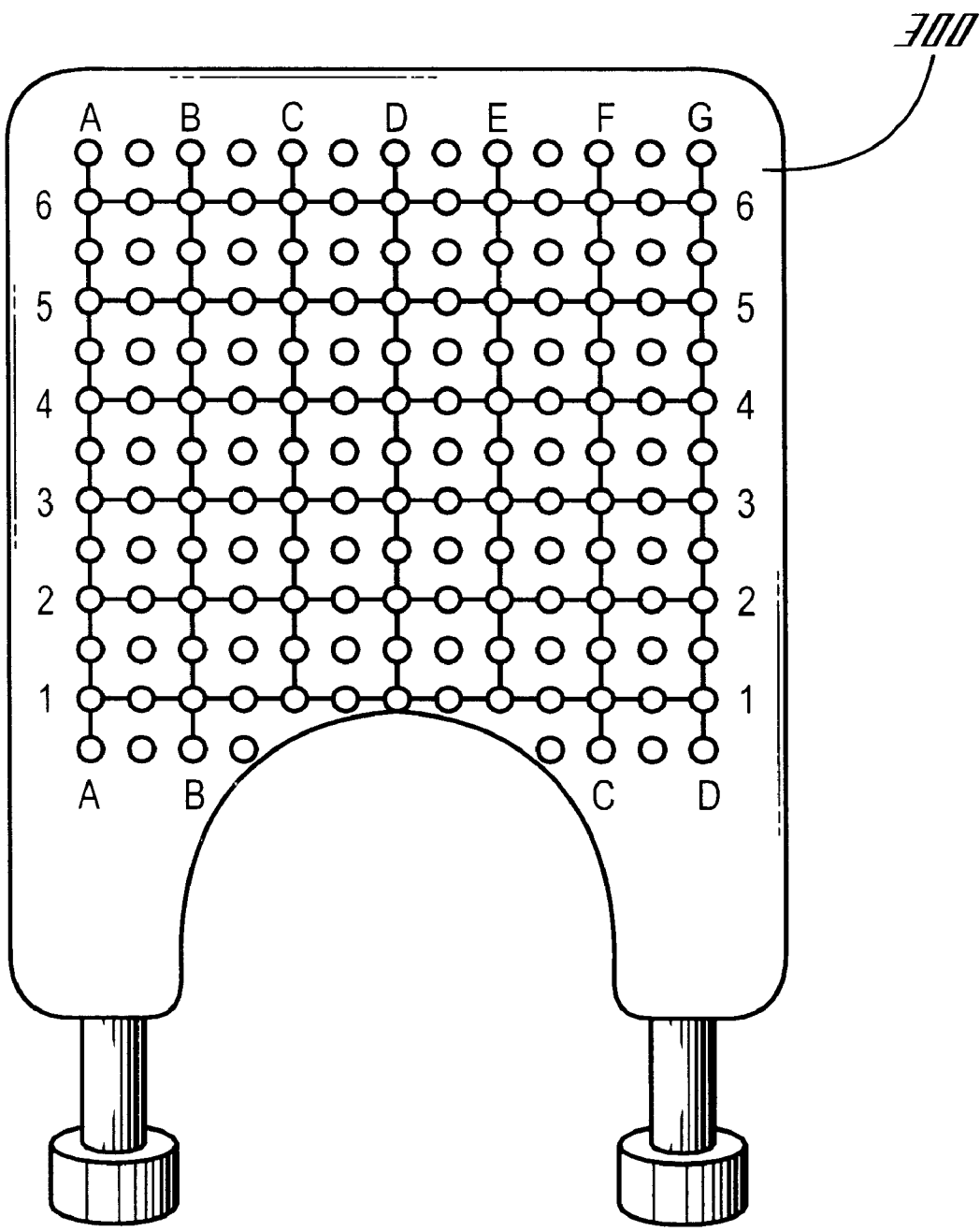
Figure 4:
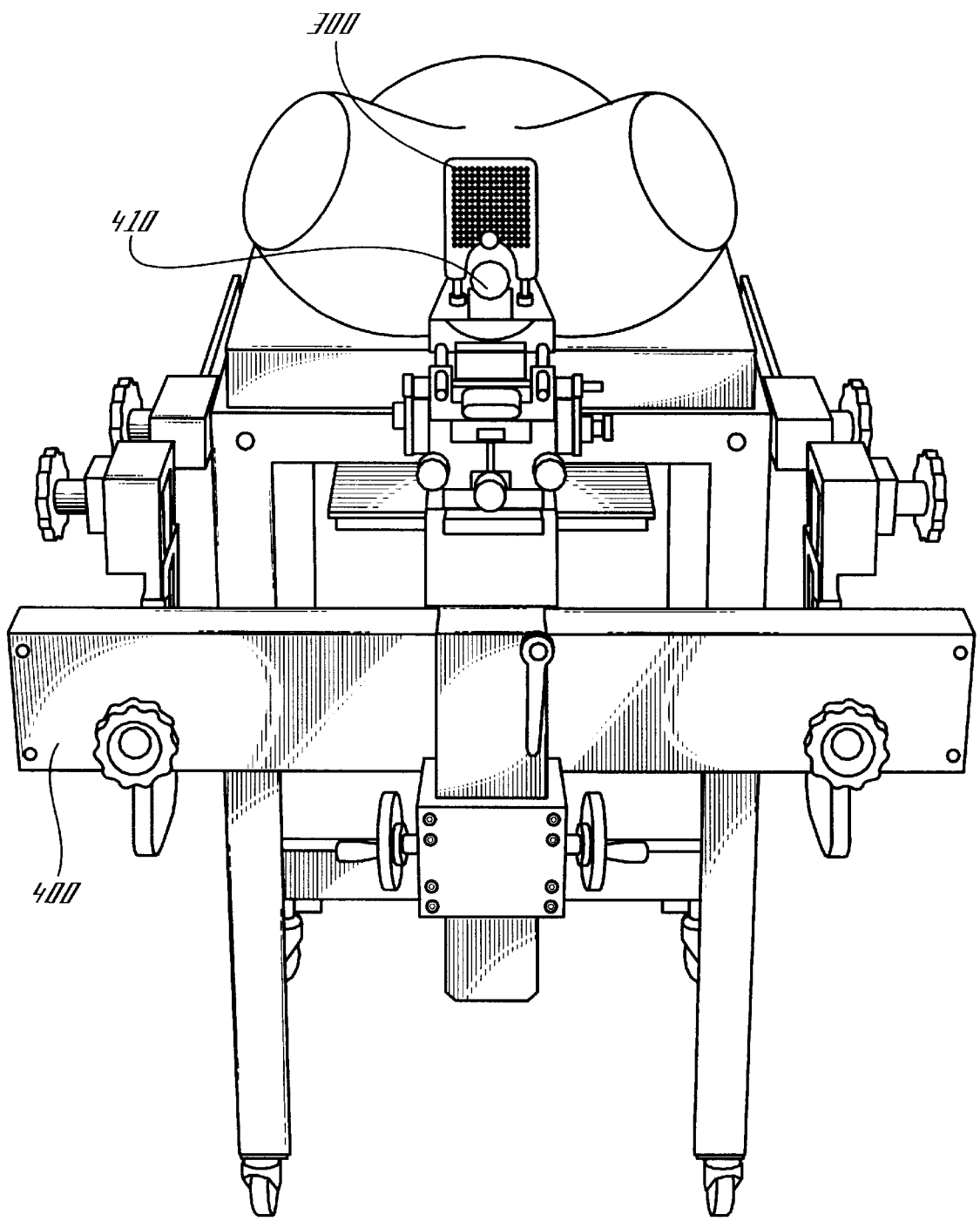
FIG. 4 is a front view of a transperineal implantation device with the template of FIG. 3.

To visualize one instance of this, FIG. 1a and 1b illustrate the isodose curves for Patient 8 for the branch-and-bound and genetic methods. In each frame of FIG. 1a and 1b, the prostate contour is denoted by the dotted line, and the isodose curves for four distinct dose levels (0.5, 1.0, 1.5, and 2.0 times the prescription dose) are shown as solid lines. The character "S" is used to denote the position of a seed. The left panels show the isodose curves associated with the plan obtained via the branch-and-bound algorithm, and the right panels show the curves associated with the plan obtained via the genetic algorithm. Patient 8 provides an illustration of a trade-off that occurred in several cases: the percentage of contour points receiving 100% of the prescription dose is lower for the plan obtained from the branch-and-bound algorithm than for the plan obtained from the genetic algorithm (80% versus 93%), while the percentage of points receiving less than 115% of the prescription dose is higher for the plan obtained via the branch-and-bound algorithm (55% versus 38%). Again, this suggests that the branch-and-bound approach may provide better control on irradiation to healthy tissue. In both cases, the prescription isodose curves conform quite well to the prostate contours in slices 1–5 and less well in slices 6 and 7. However, careful inspection reveals that the prescription isodose curves in the left panel conform slightly better than those in the right panel. In addition, the areas enclosed by the 50% isodose curves are consistently smaller in the left panel.

TABLE 3

| | | Branch-and-Bound | | | | | Genetic Algorithm | | | | |
|---|---|---|---|---|---|---|---|---|---|---|---|
| | Activity | Contour Percentage of Points Achieving | | | Uniformity | No. | Contour Percentage of Points Achieving | | | Uniformity | No. |
| Pat. | (mCi) | ≧100% | ≦115% | ≧250% | ≧100% | Seeds | ≧100% | ≦115% | ≧250% | ≧100% | Seeds |
| | | | | | 100 Gy | | | | | | |
| 1 | 0.592 | 77.5 | 50.8 | 2.02 | 97.3 | 40 | 76.5 | 54.4 | 3.70 | 96.1 | 40 |
| 2 | 0.450 | 85.2 | 60.8 | 0.96 | 99.4 | 51 | 94.8 | 41.3 | 3.85 | 99.6 | 54 |
| 3 | 0.334 | 73.2 | 50.9 | 3.26 | 94.5 | 51 | 71.6 | 57.6 | 3.26 | 93.2 | 50 |
| 4 | 0.400 | 87.3 | 55.0 | 2.16 | 98.5 | 42 | 83.2 | 46.7 | 6.47 | 97.5 | 42 |
| 5 | 0.590 | 80.5 | 52.8 | 1.08 | 98.5 | 50 | 84.8 | 46.1 | 2.48 | 97.1 | 51 |
| 6 | 0.450 | 86.4 | 48.3 | 2.69 | 98.6 | 64 | 87.5 | 43.6 | 7.47 | 98.7 | 62 |
| 7 | 0.400 | 90.1 | 43.5 | 4.80 | 97.0 | 39 | 84.8 | 43.9 | 7.58 | 96.1 | 38 |
| 8 | 0.450 | 80.0 | 55.2 | 1.85 | 98.3 | 44 | 93.0 | 37.6 | 4.85 | 99.4 | 46 |
| 9 | 0.500 | 90.0 | 43.4 | 2.22 | 98.8 | 32 | 90.8 | 39.7 | 6.39 | 98.0 | 32 |
| | | | | | 120 Gy | | | | | | |
| 10 | 0.468 | 81.3 | 42.6 | 1.15 | 93.9 | 28 | 72.8 | 59.0 | 4.60 | 92.7 | 28 |
| | | | | | 160 Gy | | | | | | |
| 11 | 0.520 | 75.5 | 58.0 | 0.87 | 96.4 | 85 | 72.4 | 52.9 | 3.47 | 94.2 | 82 |
| 12 | 0.544 | 75.6 | 48.8 | 2.85 | 95.1 | 58 | 73.9 | 48.7 | 5.69 | 93.0 | 56 |
| 13 | 0.450 | 81.1 | 59.5 | 0.47 | 98.6 | 70 | 85.7 | 51.0 | 3.26 | 98.4 | 70 |
| 14 | 0.450 | 86.4 | 61.7 | 1.30 | 98.9 | 76 | 90.5 | 48.9 | 4.47 | 98.6 | 76 |
| 15 | 0.550 | 84.1 | 38.3 | 4.55 | 98.0 | 42 | 89.6 | 29.2 | 11.04 | 98.3 | 44 |
| 16 | 0.592 | 78.0 | 53.6 | 0.62 | 97.5 | 57 | 71.1 | 62.2 | 3.71 | 96.0 | 55 |
| 17 | 0.463 | 42.6 | 73.3 | 0.84 | 87.4 | 72 | 43.4 | 73.4 | 1.25 | 84.9 | 71 |
| 18 | 0.500 | 81.0 | 45.0 | 4.39 | 97.0 | 51 | 86.3 | 41.5 | 8.55 | 98.0 | 51 |
| 19 | 0.450 | 76.8 | 55.5 | 2.80 | 96.4 | 48 | 80.1 | 50.9 | 6.44 | 97.1 | 49 |
| 20 | 0.400 | 79.2 | 52.1 | 4.73 | 97.7 | 57 | 76.9 | 53.6 | 5.36 | 96.6 | 55 |

Although differences between the measured results of the two algorithms are small, one trend is consistent: the percentage of contour points exceeding 250% of the prescription dose is smaller in every case for plans obtained from the FIG. 2 provides a graphical view of some of the data displayed in Table 3, plus data from a third approach—branch-and-bound applied to (MIP B1). The fact that case 17 was difficult for all approaches stands out. Barring this one exception, the frame on the lower right shows that all methods provided adequate coverage to the prostate—as measured by the percentage of uniformity points achieving at least 100% of the prescription dose (PrDose). It is also apparent from the lower left frame that (MIP A3 GA) (the genetic algorithm applied to (MIP A3)) yields a consistently higher percentage of contour points with dose value exceeding 250% of the prescription dose than either of the other two methods. In contrast, from the upper right frame, the percentage of contour points achieving a dose level less than 115% of the prescription dose was generally smallest for plans associated with (MIP B1 BB) (the branch-and-bound algorithm applied to (MIP B1)). These last two observations suggest that, among the three approaches, the gradient of the isodose contours associated with dose levels less than the prescription dose is generally steepest for (MIP A1 BB).

The mixed integer programming framework provides a very versatile environment for modeling brachytherapy treatment planning. The results of the numerical experiments presented herein show that this modeling paradigm coupled with appropriate optimization algorithms produce high-quality treatment plans in a fraction of the time (5–15 minutes) required by a human planner using traditional manual approaches (upwards of 4 hours). Although the results disclosed herein were not directly compared to those produced via manual approaches, based on the judgment of an experienced urologist and radiation oncologist, the computerized methods herein yield plans which use fewer seeds, provide better dose homogeneity within the target volume and lower irradiation to nearby external healthy tissue than plans obtained via manual methods.

While the invention has been described in detail in connection with the preferred embodiments known at the time, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Accordingly, the invention is not to be seen as limited by the foregoing description, but is only limited by the scope of the appended claims.

What is claimed is:

1. A method for planning the placement of seeds for the brachytherapy treatment of diseased tissue using a treatment planning model formulated as a mixed integer program, the method comprising the steps of:
   representing a placement or non-placement of a seed in each point of a predetermined three dimensional placement grid of potential seed locations with a binary indicator variable;
   representing a tumor and surrounding tissue as a predetermined three dimensional tissue grid having a plurality of tissue points;
   associating an upper bound and a lower bound for an amount of radiation received with each point in the tissue grid;
   calculating an objective value representing whether the radiation received by the tissue points as a result of a placement of seeds adheres to the upper and lower bounds; and
   selecting a placement of seeds based upon the objective value, wherein the selecting step is performed using a branch-and-bound method.

2. The method of claim 1, wherein the placement grid represents the intersection of a rectangular grid of a needle template used to place the seeds with a series of transverse planes corresponding to images formed by an imaging device.

3. The method of claim 2, wherein the imaging device is an ultrasound device.

4. The method of claim 1, wherein the distances between neighboring points in the tissue grid is the same as the distance between neighboring points in the placement grid.

5. The method of claim 1, wherein the distances between neighboring points in the tissue grid is smaller than the distance between neighboring points in the placement grid.

6. The method of claim 1, wherein the distances between neighboring points in the tissue grid is larger than the distance between neighboring points in the placement grid.

7. The method of claim 1, wherein the tissue grid includes uniformity points and contour points.

8. The method of claim 1, wherein the objective value is calculated using predetermined non-negative weights associated with each of the tissue points, the weights for a tissue point being dependent upon a comparison of the radiation received by a tissue point with the upper and lower bound for that tissue point.

9. The method of claim 8, wherein the weights for each tissue point are the same.

10. The method of claim 8, wherein the weights for a tissue point representing a type of tissue depend on the volume of the type of tissue relative to an entire target volume to be irradiated.

11. The method of claim 8, wherein the weights for a tissue point representing an anatomical structure are inversely proportional to the volume of the anatomical structure relative to an entire target volume to be irradiated.

12. The method of claim 8, wherein the weights for tissue points in an anatomical structure depend upon an importance of satisfying associated dose bounds compared to an importance of satisfying dose bounds for other anatomical structures.

13. The method of claim 8, wherein the wherein the tissue grid includes uniformity points and contour points and the weights are greater for the contour points.

14. The method of claim 8, wherein all of the weights are greater than zero.

15. The method of claim 1, wherein the selecting step is performed by selecting a placement of seeds for which the objective value is optimized by maximizing a sum of rewards associated with achieving the upper and lower bounds.

16. The method of claim 8, wherein the selecting step is performed by selecting a placement of seeds for which the objective value is optimized by maximizing a sum of rewards associated with achieving the upper and lower bounds, and the reward for each tissue point is weighted by either a first weight, a second weight or a third weight, the first weight representing a reward for satisfying the lower bound, the second weight representing a reward for satisfying the upper bound, and the third weight representing a reward for satisfying both the upper and lower bound.

17. The method of claim 1, wherein the selecting step is performed by selecting a placement of seeds for which the objective value is optimized by minimizing a sum of penalties associated with deviating from the upper and lower bounds.

18. The method of claim 8, wherein the selecting step is performed by selecting a placement of seeds for which the objective value is optimized by minimizing a sum of penalties associated with deviating from the upper and lower bounds, and the penalty for each tissue point is weighted by either a first weight multiplied by a deviation from the lower bound or a second weight multiplied by a deviation from the upper bound, the first weight representing a penalty for failing to satisfy the lower bound and the second weight representing a penalty for failing to satisfy the upper bound.

19. The method of claim 16, wherein all tissue points are weighted equally.

20. The method of claim 16, wherein the tissue grid includes different types of points including uniformity points, contour points, and points representing healthy tissue, and the weights associated with each type of point are different.

21. The method of claim 18, wherein all tissue points are weighted equally.

22. The method of claim 18, wherein the tissue grid includes different types of points including uniformity points, contour points, and points representing healthy tissue, and the weights associated with each type of point are different.

23. A method for planning the placement of seeds for the brachytherapy treatment of diseased tissue using a treatment planning model formulated as a mixed integer program, the method comprising the steps of:
  representing a placement or non-placement of a seed in each point of a predetermined three dimensional placement grid of potential seed locations with a binary indicator variable;
  representing a tumor and surrounding tissue as a predetermined three dimensional tissue grid having a plurality of tissue points;
  associating an upper bound and a lower bound for an amount of radiation received with each point in the tissue grid;
  calculating an objective value representing whether the radiation received by the tissue points as a result of a placement of seeds adheres to the upper and lower bounds; and
  selecting a placement of seeds based upon the objective value, wherein the selecting step is performed by selecting a placement of seeds for which the objective value is optimized by maximizing a sum of rewards associated with achieving the upper and lower bounds.

24. The method of claim 23, wherein the selecting step is performed using a branch-and-bound method.

25. The method of claim 23, wherein the selecting step is performed using a genetic method.

26. The method of claim 23, wherein the genetic method includes elitism.

27. The method of claim 23, wherein the seeds are placed in diseased tissue.

28. A method for planning the placement of seeds for the brachytherapy treatment of diseased tissue using a treatment planning model formulated as a mixed integer program, the method comprising the steps of:
  representing a placement or non-placement of a seed in each point of a predetermined three dimensional placement grid of potential seed locations with a binary indicator variable;
  representing a tumor and surrounding tissue as a predetermined three dimensional tissue grid having a plurality of tissue points;
  associating an upper bound and a lower bound for an amount of radiation received with each point in the tissue grid;
  calculating an objective value representing whether the radiation received by the tissue points as a result of a placement of seeds adheres to the upper and lower bounds; and
  selecting a placement of seeds based upon the objective value, wherein the selecting step is performed by selecting a placement of seeds for which the objective value is optimized by minimizing a sum of penalties associated with deviating from the upper and lower bounds.

29. The method of claim 28, wherein the selecting step is performed using a branch-and-bound method.

30. The method of claim 28, wherein the selecting step is performed using a genetic method.

31. The method of claim 28, wherein the genetic method includes elitism.

32. The method of claim 28, wherein the seeds are placed in diseased tissue.

33. A method for planning the placement of seeds for the brachytherapy treatment of diseased tissue using a treatment planning model formulated as a mixed integer program, the method comprising the steps of:
  representing a placement or non-placement of a seed in each point of a predetermined three dimensional placement grid of potential seed locations with a binary indicator variable;
  representing a tumor and surrounding tissue as a predetermined three dimensional tissue grid having a plurality of tissue points;
  associating an upper bound and a lower bound for an amount of radiation received with each point in the tissue grid;
  calculating an objective value representing whether the radiation received by the tissue points as a result of a placement of seeds adheres to the upper and lower bounds; and
  selecting a placement of seeds based upon the objective value, wherein the distances between neighboring points in the tissue grid is smaller than the distance between neighboring points in the placement grid.

34. The method of claim 33, wherein the selecting step is performed using a branch-and-bound method.

35. The method of claim 33, wherein the selecting step is performed using a genetic method.

36. The method of claim 33, wherein the genetic method includes elitism.

37. The method of claim 33, wherein the seeds are placed in diseased tissue.

38. A method for planning the placement of seeds for the brachytherapy treatment of diseased tissue using a treatment planning model formulated as a mixed integer program, the method comprising the steps of:
  representing a placement or non-placement of a seed in each point of a predetermined three dimensional placement grid of potential seed locations with a binary indicator variable;
  representing a tumor and surrounding tissue as a predetermined three dimensional tissue grid having a plurality of tissue points;
  associating an upper bound and a lower bound for an amount of radiation received with each point in the tissue grid;
  calculating an objective value representing whether the radiation received by the tissue points as a result of a placement of seeds adheres to the upper and lower bounds; and
  selecting a placement of seeds based upon the objective value, wherein the distances between neighboring points in the tissue grid is larger than the distance between neighboring points in the placement grid.

39. The method of claim 38, wherein the selecting step is performed using a branch-and-bound method.

40. The method of claim 38, wherein the selecting step is performed using a genetic method.

41. The method of claim 38, wherein the genetic method includes elitism.

42. The method of claim 38, wherein the seeds are placed in diseased tissue.

43. A computer system for planning the placement of seeds for the brachytherapy treatment of a tumor, the computer system comprising:
   a processor, and
   a memory connected to the processor,
   wherein the processor is configured to perform the steps of:
      representing a placement or non-placement of a seed in each point of a predetermined three dimensional placement grid of potential seed locations with a binary indicator variable;
      representing a tumor and surrounding tissue as a predetermined three dimensional tissue grid;
      associating an upper bound and a lower bound for an amount of radiation received with each point in the tissue grid;
      calculating an objective value representing a measure of how well the radiation received by the tissue points as a result of a placement of seeds adheres to the upper and lower bounds; and
      selecting a placement of seeds based upon the objective value, wherein the selecting step is performed using a branch-and-bound method.

44. The computer system of claim 43, wherein the placement grid represents the intersection of a rectangular grid of a needle template used to place the seeds with a series of transverse planes corresponding to images formed by an imaging device.

45. The computer system of claim 44, wherein the imaging device is an ultrasound device.

46. The computer system of claim 43, wherein the distances between neighboring points in the tissue grid is the same as the distance between neighboring points in the placement grid.

47. The computer system of claim 43, wherein the distances between neighboring points in the tissue grid is smaller than the distance between neighboring points in the placement grid.

48. The computer system of claim 43, wherein the distances between neighboring points in the tissue grid is larger than the distance between neighboring points in the placement grid.

49. The computer system of claim 43, wherein the tissue grid includes uniformity points and contour points.

50. A computer readable medium having stored thereon sequences of instructions for causing a processor to perform the steps of:
   representing a placement or non-placement of a seed in each point of a predetermined three dimensional placement grid of potential seed locations with a binary indicator variable;
   representing a tumor and surrounding tissue as a predetermined three dimensional tissue grid;
   associating an upper bound and a lower bound for an amount of radiation received with each point in the tissue grid;
   calculating an objective value representing a measure of how well the radiation received by the tissue points as a result of a placement of seeds adheres to the upper and lower bounds; and
   selecting a placement of seeds based upon the objective value, wherein selecting is performed using a branch-and-bound method.

51. The computer readable medium of claim 50, wherein the objective value is calculated using predetermined non-negative weights associated with each of the tissue points, the weights for a tissue point being dependent upon a comparison of the radiation received by a tissue point with the upper and lower bound for that tissue point.

52. The computer readable medium of claim 51, wherein the weights for each tissue point are the same.

53. The computer readable medium of claim 51, wherein the weights for a tissue point representing a type of tissue depend on the volume of the type of tissue relative to an entire target volume to be irradiated.

54. The computer readable medium of claim 51, wherein the weights for a tissue point representing an anatomical structure are inversely proportional to the volume of the anatomical structure relative to an entire target volume to be irradiated.

55. The computer readable medium of claim 51, wherein the weights for tissue points in an anatomical structure depend upon an importance of satisfying associated dose bounds compared to an importance of satisfying dose bounds for other anatomical structures.

56. The computer readable medium of claim 51, wherein the wherein the tissue grid includes uniformity points and contour points and the weights are greater for the contour points.

57. The computer readable medium of claim 51, wherein all of the weights are greater than zero.

58. The computer readable medium of claim 51, wherein the selecting step is performed by selecting a placement of seeds for which the objective value is optimized by maximizing a sum of rewards associated with achieving the upper and lower bounds, and the reward for each tissue point is weighted by either a first weight, a second weight or a third weight, the first weight representing a reward for satisfying the lower bound, the second weight representing a reward for satisfying the upper bound, and the third weight representing a reward for satisfying both the upper and lower bound.

59. The computer readable medium of claim 51, wherein the selecting step is performed by selecting a placement of seeds for which the objective value is optimized by minimizing a sum of penalties associated with deviating from the upper and lower bounds, and the penalty for each tissue point is weighted by either a first weight multiplied by a deviation from the lower bound or a second weight multiplied by a deviation from the upper bound, the first weight representing a penalty for failing to satisfy the lower bound and the second weight representing a penalty for failing to satisfy the upper bound.

60. The computer readable medium of claim 58, wherein all tissue points are weighted equally.

61. The computer readable medium of claim 58, wherein the tissue grid includes different types of points including uniformity points, contour points, and points representing healthy tissue, and the weights associated with each type of point are different.

62. The computer readable medium of claim 51, wherein all tissue points are weighted equally.

63. The computer readable medium of claim 51, wherein the tissue grid includes different types of points including uniformity points, contour points, and points representing healthy tissue, and the weights associated with each type of point are different.

64. A method for treating diseased tissue using a treatment planning model formulated as a mixed integer program comprising the steps of:

representing a placement or non-placement of a seed in each point of a predetermined three dimensional placement grid of potential seed locations with a binary indicator variable;

representing a tumor and surrounding tissue as a predetermined three dimensional tissue grid;

associating an upper bound and a lower bound for an amount of radiation received with each point in the tissue grid;

calculating an objective value representing whether the radiation received by the tissue points as a result of a placement of seeds adheres to the upper and lower bounds; and selecting a placement of seeds based upon the objective value, wherein selecting is performed using a branch-and-bound method.

65. The method of claim 64, wherein the placement grid represents the intersection of a rectangular grid of a needle template used to place the seeds with a series of transverse planes corresponding to images formed by an imaging device.

66. The method of claim 65, wherein the imaging device is an ultrasound device.

67. The method of claim 64, wherein the distances between neighboring points in the tissue grid is the same as the distance between neighboring points in the placement grid.

68. The method of claim 64, wherein the distances between neighboring points in the tissue grid is smaller than the distance between neighboring points in the placement grid.

69. The method of claim 64, wherein the distances between neighboring points in the tissue grid is larger than the distance between neighboring points in the placement grid.

70. The method of claim 64, wherein the tissue grid includes uniformity points and contour points.

71. A method for treating diseased tissue using a treatment planning model formulated as a mixed integer program comprising the steps of:

representing a placement or non-placement of a seed in each point of a predetermined three dimensional placement grid of potential seed locations with a binary indicator variable;

representing a tumor and surrounding tissue as a predetermined three dimensional tissue grid;

associating an upper bound and a lower bound for an amount of radiation received with each point in the tissue grid;

calculating an objective value representing whether the radiation received by the tissue points as a result of a placement of seeds adheres to the upper and lower bounds; and selecting a placement of seeds based upon the objective value, wherein selecting is performed by selecting a placement of seeds for which the objective value is optimized by maximizing a sum of rewards associated with achieving the upper and lower bounds.

72. The method of claim 71, wherein the selecting step is performed using a branch-and-bound method.

73. The method of claim 71, wherein the selecting step is performed using a genetic method.

74. The method of claim 71, wherein the genetic method includes elitism.

75. The method of claim 71, wherein the seeds are placed in diseased tissue.

76. A method for treating diseased tissue using a treatment planning model formulated as a mixed integer program comprising the steps of:

representing a placement or non-placement of a seed in each point of a predetermined three dimensional placement grid of potential seed locations with a binary indicator variable;

representing a tumor and surrounding tissue as a predetermined three dimensional tissue grid;

associating an upper bound and a lower bound for an amount of radiation received with each point in the tissue grid;

calculating an objective value representing whether the radiation received by the tissue points as a result of a placement of seeds adheres to the upper and lower bounds; and selecting a placement of seeds based upon the objective value, wherein selecting is performed by selecting a placement of seeds for which the objective value is optimized by minimizing a sum of penalties associated with deviating from the upper and lower bounds.

77. The method of claim 76, wherein the objective value is calculated using predetermined non-negative weights associated with each of the tissue points, the weights for a tissue point being dependent upon a comparison of the radiation received by a tissue point with the upper and lower bound for that tissue point.

78. The method of claim 77, wherein the weights for each tissue point are the same.

79. The method of claim 77, wherein the weights for a tissue point representing a type of tissue depend on the volume of the type of tissue relative to an entire target volume to be irradiated.

80. The method of claim 77, wherein the weights for a tissue point representing an anatomical structure are inversely proportional to the volume of the anatomical structure relative to an entire target volume to be irradiated.

81. The method of claim 77, wherein the weights for tissue points in an anatomical structure depend upon an importance of satisfying associated dose bounds compared to an importance of satisfying dose bounds for other anatomical structures.

82. The method of claim 77, wherein the wherein the tissue grid includes uniformity points and contour points and the weights are greater for the contour points.

83. The method of claim 77, wherein all of the weights are greater than zero.

84. The method of claim 77, wherein the selecting step is performed by selecting a placement of seeds for which the objective value is optimized by maximizing a sum of rewards associated with achieving the upper and lower bounds, and the reward for each tissue point is weighted by either a first weight, a second weight or a third weight, the first weight representing a reward for satisfying the lower bound, the second weight representing a reward for satisfying the upper bound, and the third weight representing a reward for satisfying both the upper and lower bound.

85. The method of claim 77, wherein the selecting step is performed by selecting a placement of seeds for which the objective value is optimized by minimizing a sum of penalties associated with deviating from the upper and lower bounds, and the penalty for each tissue point is weighted by either a first weight multiplied by a deviation from the lower bound or a second weight multiplied by a deviation from the upper bound, the first weight representing a penalty for failing to satisfy the lower bound and the second weight representing a penalty for failing to satisfy the upper bound.

86. The method of claim 84, wherein all tissue points are weighted equally.

87. The method of claim 84, wherein the tissue grid includes different types of points including uniformity points, contour points, and points representing healthy tissue, and the weights associated with each type of point are different.

88. The method of claim 77, wherein all tissue points are weighted equally.

89. The method of claim 77, wherein the tissue grid includes different types of points including uniformity points, contour points, and points representing healthy tissue, and the weights associated with each type of point are different.

* * * * *